United States Patent
Yow et al.

(10) Patent No.: US 9,550,054 B2
(45) Date of Patent: Jan. 24, 2017

(54) SAFETY LUER CONNECTION

(75) Inventors: D. Gregory Yow, Wake Forest, NC (US); Jonathan Walborn, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 957 days.

(21) Appl. No.: 13/287,043

(22) Filed: Nov. 1, 2011

(65) Prior Publication Data

US 2012/0046650 A1 Feb. 23, 2012

Related U.S. Application Data

(63) Continuation of application No. 11/765,894, filed on Jun. 20, 2007, now Pat. No. 8,070,189.

(51) Int. Cl.
*A61M 39/10* (2006.01)

(52) U.S. Cl.
CPC ...... *A61M 39/10* (2013.01); *A61M 2039/1027* (2013.01); *A61M 2039/1094* (2013.01); *A61M 2205/6045* (2013.01)

(58) Field of Classification Search
USPC ............ 285/332, 332.1, 374, 399, 401, 402; 604/523, 533, 534, 535
See application file for complete search history.

(56) References Cited

U.S. PATENT DOCUMENTS

| | | | |
|---|---|---|---|
| 803,127 A | 10/1905 | Palmer | |
| 4,511,359 A | 4/1985 | Vaillancourt | |
| 4,600,015 A * | 7/1986 | Evans et al. | 600/593 |
| 4,619,640 A | 10/1986 | Potolsky et al. | |
| 4,668,217 A | 5/1987 | Isono | |
| 5,059,170 A * | 10/1991 | Cameron | 604/43 |
| 5,123,840 A * | 6/1992 | Nates | 433/95 |
| 5,437,650 A | 8/1995 | Larkin et al. | |
| 5,632,735 A | 5/1997 | Wyatt et al. | |
| 5,782,505 A | 7/1998 | Brooks et al. | |
| 5,810,792 A | 9/1998 | Fangrow et al. | |
| 5,964,785 A | 10/1999 | Desecki et al. | |

(Continued)

FOREIGN PATENT DOCUMENTS

| | | |
|---|---|---|
| DE | 298 18 311 | 1/1999 |
| DE | 101 40 292 | 3/2003 |

(Continued)

*Primary Examiner* — Daniel P Stodola
*Assistant Examiner* — Fannie Kee
(74) *Attorney, Agent, or Firm* — McDermott Will & Emery LLP (57) ABSTRACT

A connection device has a male connector and a female connector. The female connector will only accommodate the dedicated male connector, thereby prohibiting a misconnection with the wrong male connector. In certain embodiments, a member prohibits male connectors, other than a dedicated male connector, from being inserted into the female connector. In certain other embodiments, a post prohibits male connectors, other than a dedicated male connector including a slot, from being inserted into the female connector. In still certain other embodiments, a series of prongs in the male connector and corresponding grooves in the female connector ensure the proper connection. Once the male connector is inserted and secured within the female connector, a fluid-tight seal is formed between the male connector and the female connector.

8 Claims, 8 Drawing Sheets

(56) References Cited

U.S. PATENT DOCUMENTS

| | | | |
|---|---|---|---|
| 6,027,482 | A | 2/2000 | Imbert |
| 6,206,849 | B1 * | 3/2001 | Martin et al. .................. 604/43 |
| 6,422,607 | B1 | 7/2002 | Kirby |
| 7,611,317 | B2 | 11/2009 | Muderlak et al. |
| 2004/0167463 | A1 * | 8/2004 | Zawacki et al. ................ 604/43 |
| 2004/0211484 | A1 | 10/2004 | Fournie et al. |
| 2005/0090805 | A1 | 4/2005 | Shaw et al. |
| 2005/0267445 | A1 * | 12/2005 | Mendels ...................... 604/534 |

FOREIGN PATENT DOCUMENTS

| | | |
|---|---|---|
| FR | 2507896 | 12/1982 |
| FR | 2863162 | 6/2005 |
| GB | 2 356 148 | 5/2001 |
| WO | WO 81/00053 | 1/1981 |
| WO | WO 03/076001 | 9/2003 |
| WO | WO 2007/030403 | 3/2007 |
| WO | WO 2007/047845 | 4/2007 |
| WO | WO 2007/104961 | 9/2007 |
| WO | WO 2008/049568 | 5/2008 |

* cited by examiner

SAFETY LUER CONNECTION

This application is a continuation of U.S. application Ser. No. 11/765,894, filed Jun. 20, 2007 and now issued as U.S. Pat. No. 8,070,189, which is hereby incorporated by reference in its entirety.

TECHNICAL FIELD

The disclosed embodiments relate to a medical connection device, and more particularly, to a male and female connection device, which can be used in conjunction with fluid administration, such as intravenous fluid administration.

BACKGROUND

Luer connections are the typical mechanisms for attaching various medical devices such as syringes, catheters, and intravenous lines to one another. These lines are then generally connected to a patient via a catheter. In a typical luer connection, male and female connectors are mated together to form and secure the connection. Luer connections are widely used in the medical industry because they are quick and easy to assemble.

However, with this ease of use comes a high risk of error. For example, in high risk connections, such as epidural lines, the connection of an incorrect line can have serious consequences, including death, for the patient. There is a high risk of accidentally connecting the wrong lines because standard luer connectors are used for both intravenous fluid and epidural infusions. Also, additional lines are commonly found near bedsides of patients seeking medical care for a variety of ailments. Thus, a male connector intended for use with an intravenous line could be easily confused for one intended for use with an epidural line. This confusion can lead to a misconnection, resulting in medication or air erroneously being delivered into an unintended site, leading to serious complications.

Currently, precautions for misconnections include double-checking the connection prior to connecting the luers. Alternatively, the different connectors and their attached lines may be specially labeled. Labeling may be accomplished by placing colored tape on the tubing, or placing a color-coded marker on the connectors themselves.

While these precautionary measures attempt to solve the problems of misconnections, all of these precautions require an active, mitigating step. This can be problematic and impractical for nurses and doctors who are often working in emergency situations and do not have the luxury of performing time-consuming cautionary steps.

Thus, there is a need for a safety luer connection, in which there is minimal or no risk of misconnecting male and female luers, and in which no additional steps are required by hospital personnel to avoid misconnections.

SUMMARY

The above and other needs are met by the disclosed embodiments which provide a connection device comprising a male connector, which includes a body with a distal end and a proximal end; and a projection. The projection has an opening located at a distal end of the projection. The opening is in fluid communication with a fluid passageway located within the body. The projection has a length L1. The connection device further comprises a female connector, comprising a body, a distal end, and a proximal end. A fluid passageway is located within the body. The female connector includes a member perpendicular to the fluid passageway within the body and positioned a length L2 from the proximal end of the female connector and blocking insertion of the projection past the member. The length L1 is approximately equal to L2, such that only a male connector with a projection having the length L1 is fully insertable into the female connector. This will prevent the insertion of typical male connectors.

Other needs are met by disclosed embodiments which provide a connection device comprising a male connector including a projection with a slot. The connection device also includes a female connector comprising a post perpendicular to the fluid passageway within the body. The post is configured to engage the corresponding slot of the projection during insertion of the male connector into the female connector and block insertion of a projection of a male connector without a slot into the female connector.

The earlier stated needs and others are met by still other disclosed embodiments which provide a connection device comprising a male connector, which includes a body with at least one prong. The male connector further includes a tubing pocking with standoffs. The standoffs are configured to permit fluid to flow through a periphery path of the tubing pocket. The male connector also includes at least one attachment piece. The connection device also comprises a female connector, including a body with at least one groove. The groove corresponds to the prong of the male connector, and aligns the male connector upon its insertion into the female connector. The female connector includes a ridge, which cooperates with the attachment piece of the male connector to secure the male connector within the female connector. The female connector further includes a tubing pocket with standoffs.

The foregoing and other features, aspects and advantages of the disclosed embodiments will become more apparent from the following detailed description and accompanying drawings.

DETAILED DESCRIPTION

It is contemplated that the subject matter described herein may be embodied in many forms. Accordingly, the embodiments described in detail below are the presently preferred embodiments, and are not to be considered as limitations.

The disclosed embodiments address problems related to the misconnection of male and female luer connection devices and the dire consequences misconnections may cause in time critical situations. The disclosed embodiments solve these problems, at least in part, by providing a connection device comprising a male connector, which includes a body with a distal end and a proximal end, and a projection from the body having an opening located at a distal end of the projection. The opening is in fluid communication with a fluid passageway located within the body. The projection has a length L1. The connection device further comprises a female connector comprising a body with a distal end and a proximal end, a fluid passageway located within the body, and a member perpendicular to the fluid passageway within the body. The member is positioned a length L2 from the proximal end of the female connector and blocks insertion of the projection past the member, with L1 approximately equal to L2, such that only a male connector with a projection having the length L1 is fully insertable into the female connector. This will prevent the insertion of typical male connectors.

The problems are also addressed by disclosed embodiments which provide a connection device comprising a male connector including a projection with a slot. The connection device also includes a female connector comprising a post perpendicular to the fluid passageway within the body. The post is configured to engage the corresponding slot of the projection during insertion of the male connector into the female connector and block insertion of a projection of a male connector without a slot into the female connector a connection device comprising a male connector including a slot. The connection device also includes a female connector comprising a post. The post is configured to engage the corresponding slot of the male connector. The post is located so as to only allow full insertion of the dedicated male connector into the female connector.

Other disclosed embodiments provide a connection device comprising a male connector, which includes a body with at least one prong. The male connector further includes a tubing pocking with standoffs. The standoffs are configured to permit fluid to flow through a periphery path of the tubing pocket. The male connector also includes at least one attachment piece. The connection device also comprises a female connector, including a body with at least one groove. The groove corresponds to the prong of the male connector, and aligns the male connector upon its insertion into the female connector. The female connector includes a ridge, which cooperates with the attachment piece of the male connector to secure the male connector within the female connector. The female connector further includes a tubing pocket with standoffs.

Figure 1:
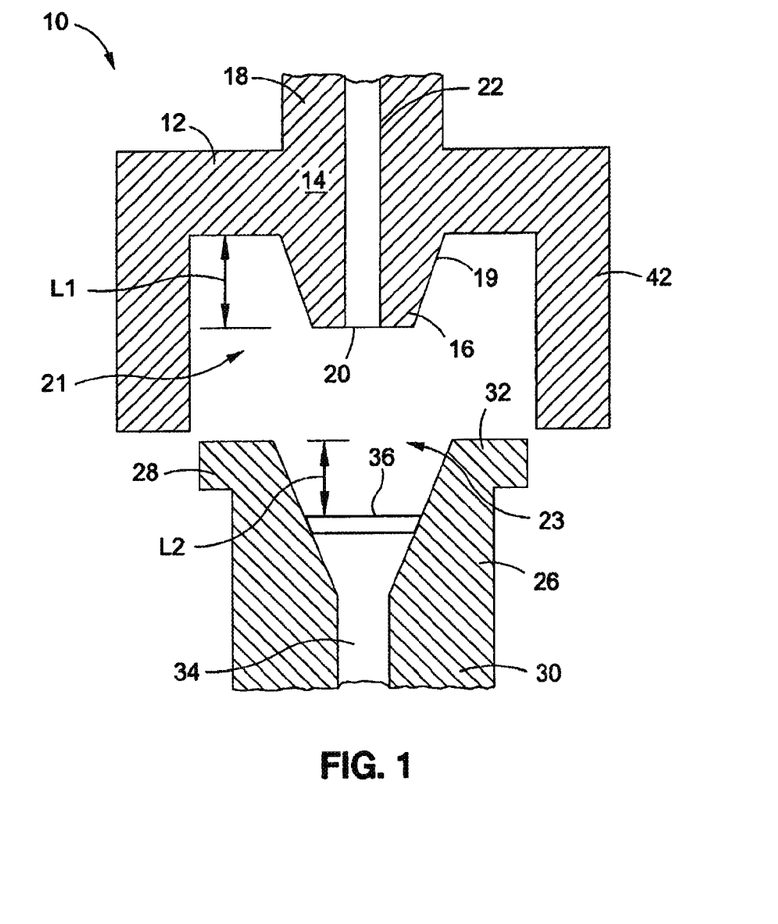
FIG. 1 is a cross-sectional view of the male connector and female connector of one embodiment of the connection device, in an unconnected state.

FIG. 1 shows a connection device 10. The device comprises a male connector 12, that includes a body 14. The body 14 has a distal end 16 and a proximal end 18. It should be noted that "distal" refers to the direction toward the patient. "Proximal" refers to the direction away from the patient, or toward the syringe or other collection or dispensing device, such as an intravenous (IV) bag. The male connector 12 has a generally cup-shaped design, as seen in FIG. 1, with a recess 21 configured to mate with a female connector. A projection 19 extends within the recess 21 towards the distal end 16 of the body 14. The projection 19 is received within a mating portion of a female connector, as will be further described. The projection 19 includes an opening 20 in fluid communication with a fluid passageway 22. Thus, fluid may flow unobstructed through the fluid passageway 22 and out of the opening 20.

The male connector 12 is configured to mate securely with the female connector 26 depicted in FIG. 1, with other male connectors not being able to be securely mated. As shown in FIG. 1, the connection device 10 further comprises a female connector 26. The female connector 26 includes a body 28. The body 28 has a distal end 30 and a proximal end 32. A fluid passageway 34 is located within the body 28. The male connector 12 of FIG. 1 may be inserted into the female connector 26 such that the fluid passageways 22, 34 are aligned with one another. The fluid passageways 22, 34 are sized to accommodate typical sized intravenous tubing. However, other types of male connectors will not be able to be fully inserted into the female connector 26.

Figure 2:
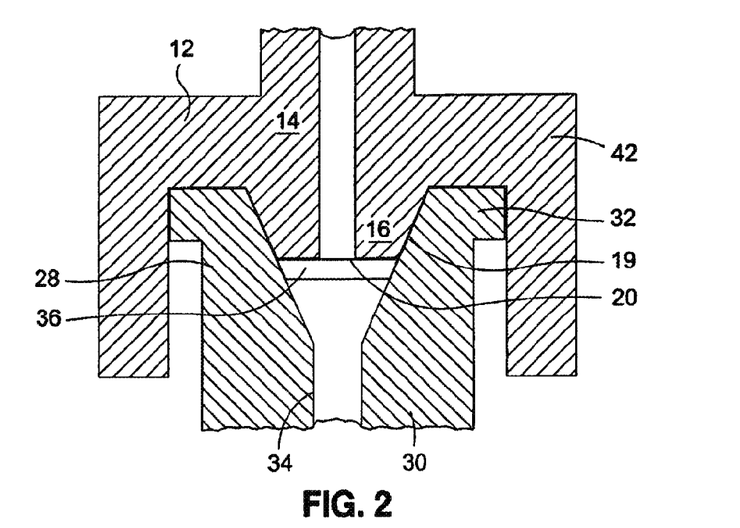
FIG. 2 is a cross-sectional view of the male connector and female connector of the connection device of FIG. 1, in a connected state.

The female connector 26 includes a member 36. The member 36 is fixedly positioned perpendicular to the fluid passageway 34 of the female connector 26. The member 36 is shallowly located, such that it is not immediately proximate to the distal end 30 of the female connector 26. The member 36 is positioned within the fluid passageway 34 so that only the dedicated male connector 12 may be fully inserted into the female connector 26, as shown in FIG. 2. The length L1 of the projection 19 is substantially equal to the length L2 between the proximal opening 23 of the female connector 26 and the member 36. Typical male connectors include projections that are longer, such that the projections extend to the distal end of the male connector.

Figure 3:
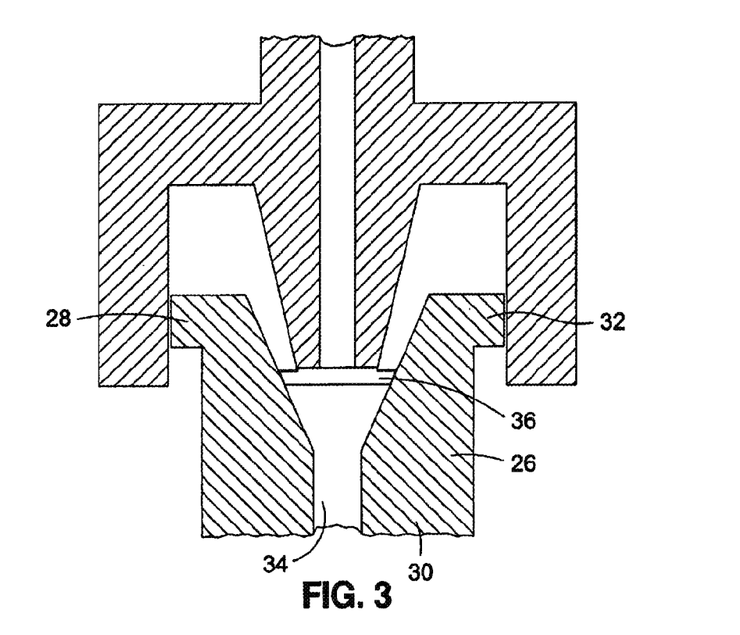
FIG. 3 is a cross-sectional view of the female connector of the connection device of FIG. 1 and a typical male luer.
Figure 4:
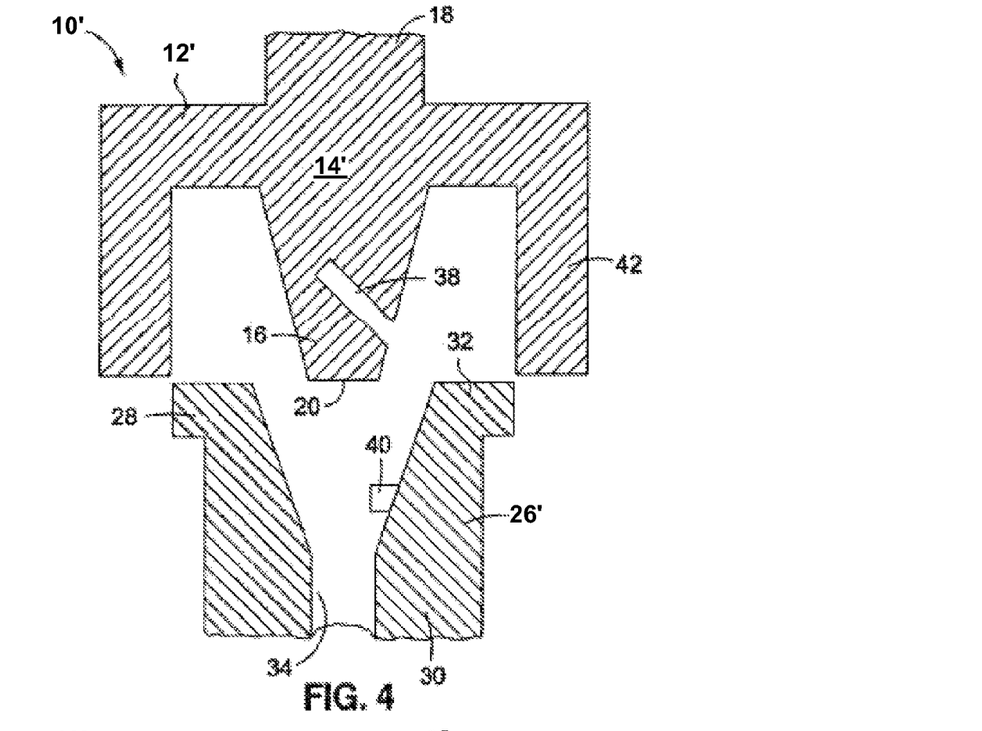
FIG. 4 is a cross-sectional view of the male connector and female connector of another embodiment of the connection device, in an unconnected state.

FIG. 3 shows an attempt to insert a typical male luer into the female connector 26. If an incorrect male connector is inserted into the female connector 26, the member 36 will prevent the connectors 12, 26 from properly mating. By contrast, with the connection made in FIG. 2 employing the dedicated male connector 12 and female connector 26, a fluid-tight seal may be formed once the male and female connectors 12, 26 are secured. The member 36 ensures an incorrect male connector cannot be fully inserted, which could be a potentially fatal situation for the patient.

In certain embodiments, the male connector 12 includes a threaded locking hub 42 and the body 28 of the female connector 26 is also threaded. Hence, the locking hub 42 may be screwed onto and around the female connector body 26, securing the male and female connectors 12, 26.

As discussed above, the member 36 of the female connector 26 prohibits insertion of an incorrect male connector 12. In addition, the female connector 26 is visually devoid of the typical locking tabs that are found on typical female connectors. This should be an additional indication that the female connector 26 disclosed is not to be used with typical male luers.

In certain other embodiments, as shown by FIGS. 4-7, the male connector 12' includes a slot 38. The slot 38 may be rotatably cut-out around the exterior of the body 14 of the male connector 12'. As shown in FIGS. 4-7, the female connector 26' includes a post 40, which may be cylindrically shaped, or may assume other shapes configured to interact with the slot. The post 40 is configured to engage the slot 38 of the male connector 12', upon insertion of the male connector 12' into the female connector 26'.

Figure 5:
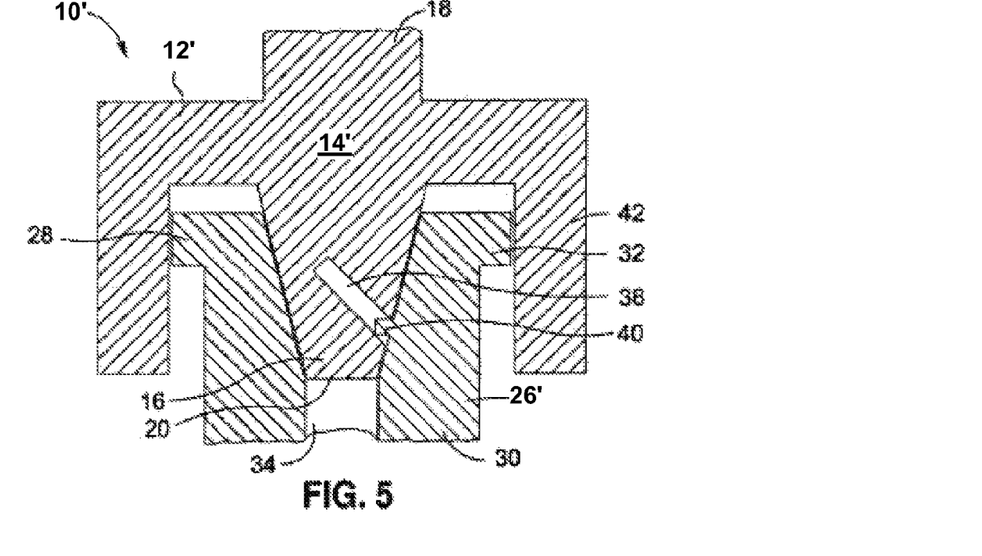
FIG. 5 is a cross-sectional view of the male connector and female connector of the connection device of FIG. 4, in a partially connected state.
Figure 6:
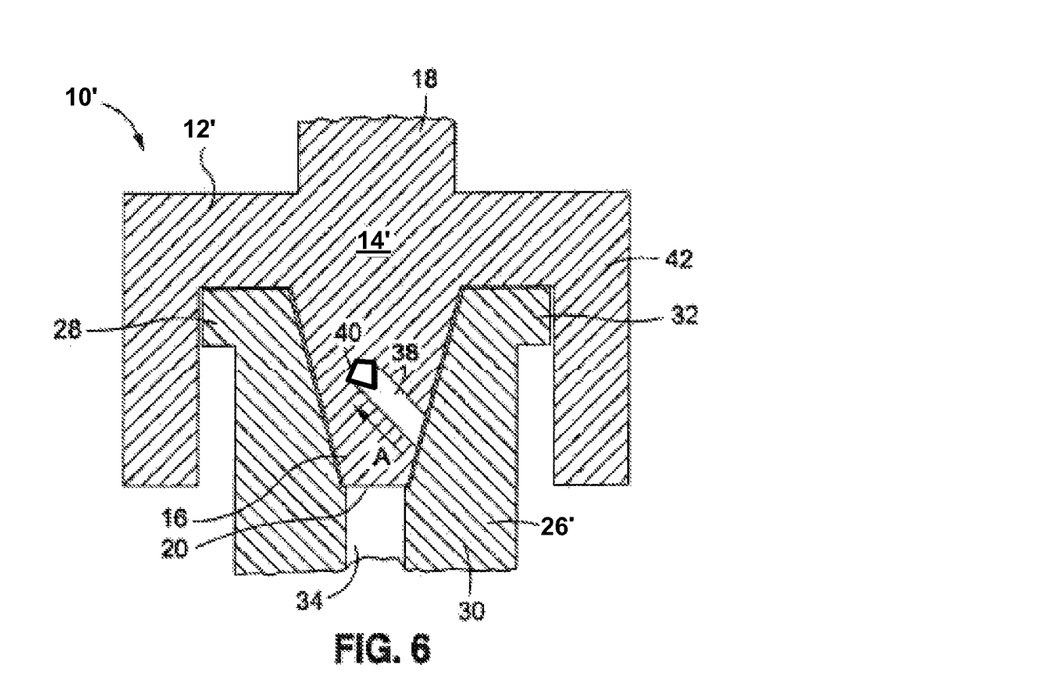
FIG. 6 is a cross-sectional view of the male connector and female connector of the connection device of FIG. 4, in a connected state.
Figure 7:
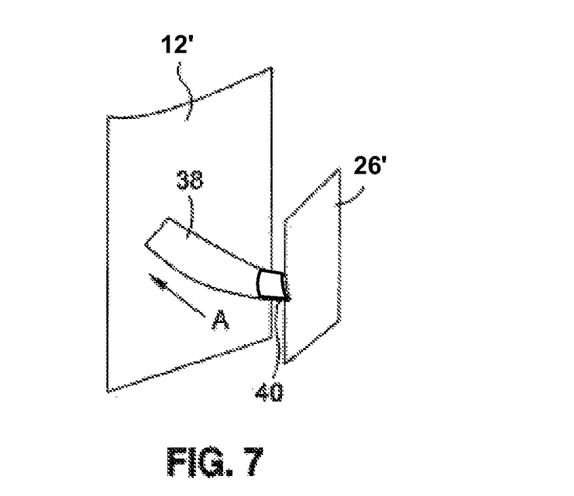
FIG. 7 is a close-up partial-perspective view of the slot and post of the connection device of FIG. 4, in a partially connected state.

As shown by FIGS. 5-7, as the male connector 12' is inserted into the female connector 26', the post 40 engages the end of the slot 38. The post 40 is shallowly located on the female connector 26'. The location of the post 40 prevents full insertion and engagement of a typical male luer. The location of the post 40 is such that it engages the slot 38 when the male connector 12' is only partially inserted, shown by FIG. 5. The male connector 12' is then rotated as it is fully inserted into the female connector 26', such that the post 40 travels up and further into the slot 38, shown in direction A in FIGS. 6 and 7.

Figure 8:
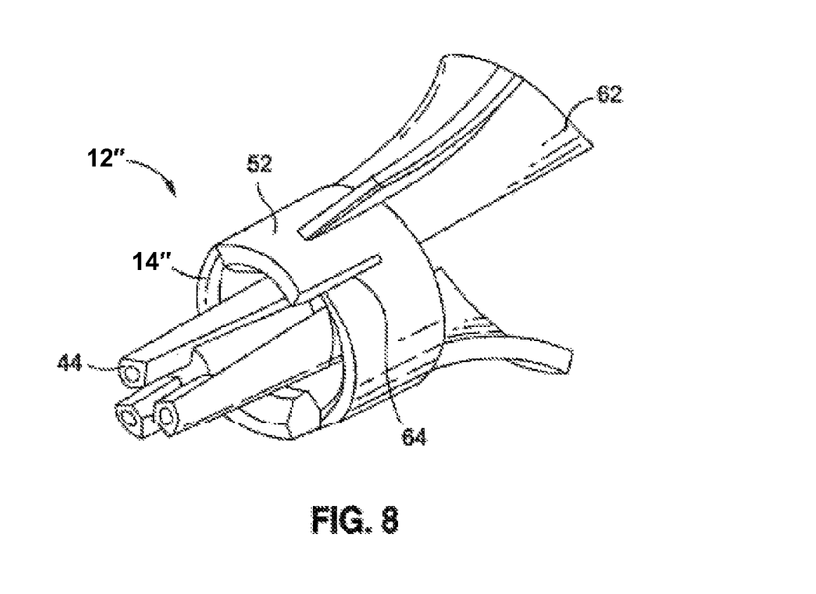
FIG. 8 is a perspective view of the male connector of another embodiment of the connection device.
Figure 9:
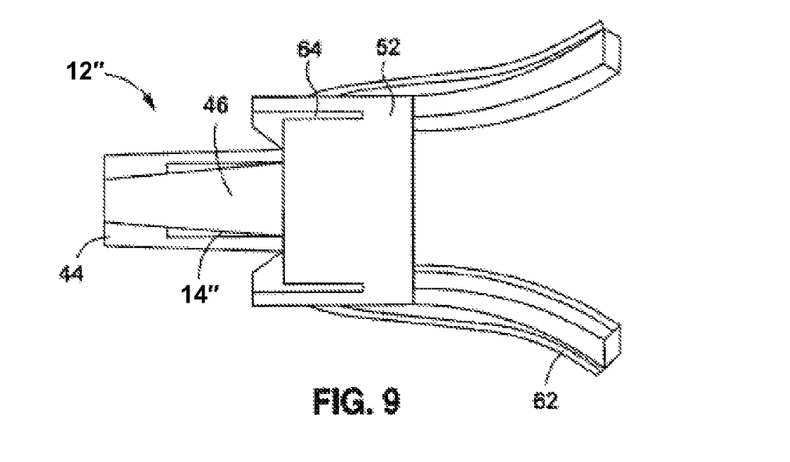
FIG. 9 is a side view of FIG. 8.
Figure 10:
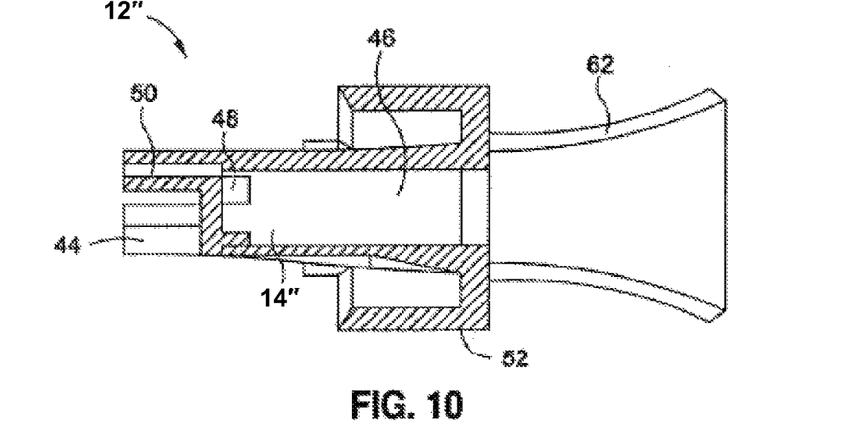
FIG. 10 is a cross-sectional view of FIG. 9.

FIGS. 8-10 show a connection device 10" comprising the male connector 12", in which the body 14" has at least one prong 44. As shown in FIG. 8, the male connector 12" includes a tubing pocket 46 with standoffs 48. The standoffs 48 are configured to permit fluid passing through the male connector 12" to flow through a periphery path 50 of the tubing pocket 46. Thus, the fluid will take a more direct path through the male connector 12". The male connector 12" further includes at least one attachment piece 52. The attachment piece 52 may be a snapping piece 52 of a snap-fit connection.

Figure 11:
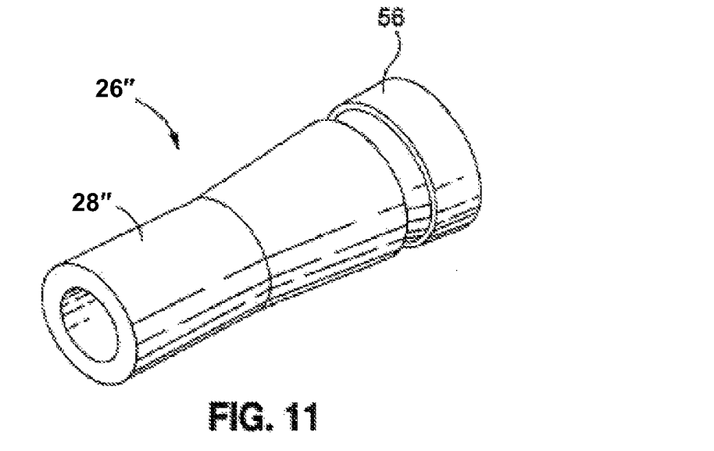
FIG. 11 is a perspective view of the female connector of the connection device of FIG. 8.
Figure 12:
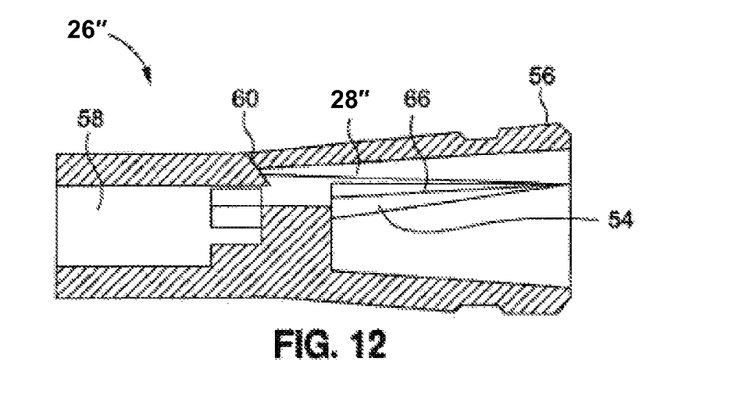
FIG. 12 is a cross-sectional view of FIG. 12.

The connection device 10" further includes the female connector 26", shown in FIGS. 11-12, in which the female connector 26" includes at least one groove 54 (FIG. 12). The groove 54 is formed between a plurality of ribs 66 located within the female connector 26". The groove 54 corresponds to the prong 44 of the male connector 12". Upon insertion of the male connector 12" into the female connector 26", the groove 54 and prong 44 matingly engage, aligning the male connector 12" within the female connector 26", shown in FIG. 13. The groove 54 is tapered so that the prong 44 will align easier with the groove 54. The male connector 12" may be rotated until the prong 44 engages the groove 54. While only one prong 44 may be present, it is contemplated that the male connector 12" comprises a plurality of prongs 44 that engage a plurality of corresponding grooves 54. The presence of the prong 44 and groove 54 prevents the connection device 10" from being compatible with typical ISO male and female luer connectors. Thus, the connection device ensures that an incorrect connector, and line, will not be attached to a patient.

Figure 13:
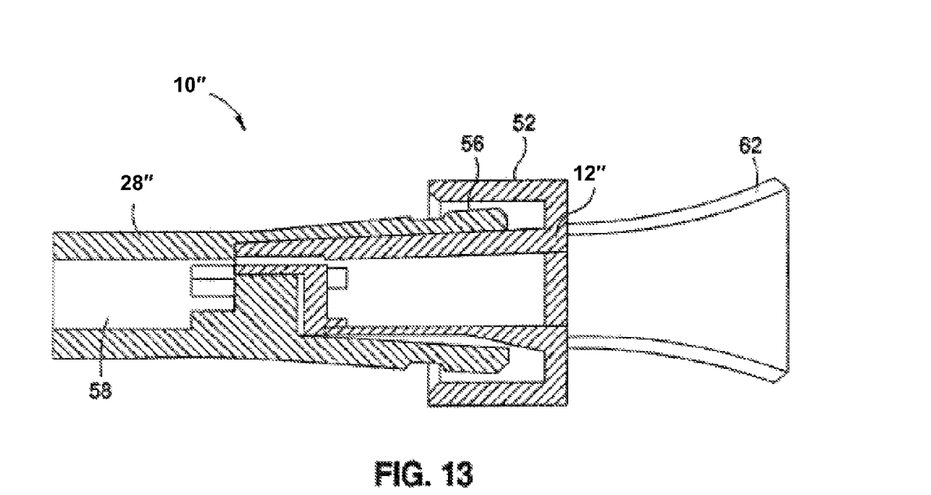
FIG. 13 is a cross-sectional view of the male and female connectors of FIGS. 8 and 11, in a connected state.

The female connector 26" also includes a ridge 56, shown in FIGS. 11 and 12. The ridge 56 cooperates with the snapping piece 52 of the male connector 12", seen in FIG. 8. Thus, as shown in FIG. 13, to secure the male and female connectors 12", 26", the snapping piece 52 snaps onto the ridge 56. This secures the connectors 12", 26" together and may form a fluid-tight seal. The bodies 14", 28" of the male and female connectors 12", 26" are generally cylindrically shaped such that they may easily be mated. However, the bodies 14", 28" may be shaped in other geometries as well.

As shown in FIG. 12, the female connector 26" further includes a tubing pocket 58 with standoffs 60. The tubing pockets 46, 58 are sized to receive typical sized intravenous tubing. The standoffs 48, 60 prevent the tubing within the tubing pockets 46, 58 from forming a seal at the base of the tubing pocket. This would prevent flow of the fluid through the connection device 10" and to the patient or fluid receptacle.

The male connector 12" may also include at least one wing 62, and the body 14" may have a notch 64. The wing 62 is shaped to extend outwardly from the body 14", as seen in FIGS. 8-10. The notch 64 provides for independent flexibility of the wing 62. Compressing the wing 62 disengages the snapping piece 52 of the male connector 12". The notch 64 allows the wing 62 to flex open and away from the body 14" of the male connector 12". This allows for removal of the male connector 12" from the female connector 26. It is contemplated that a plurality of wings 62 may be included on the male connector 12".

The attachment piece 52 of the male connector 12" may be threaded, and the ridge 56 of the female connector 26" may be threaded. Thus, to secure the male and female connectors 12", 26", the male connector 12" may be screwed onto the female connector 26".

Figure 14:
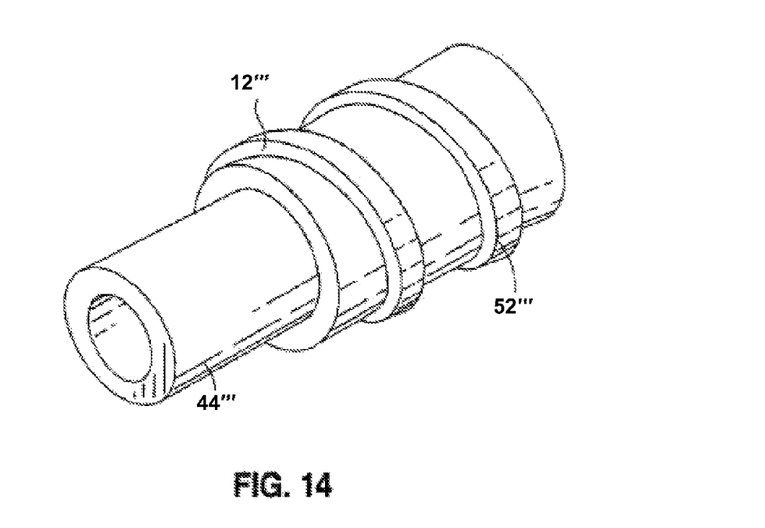
FIG. 14 is a perspective view of the male connector of another embodiment of the connection device.
Figure 15:
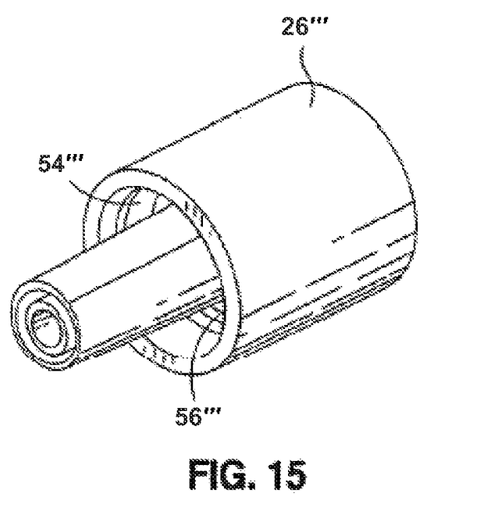
FIG. 15 is a perspective view of the female connector of the connection device of FIG. 14.
Figure 16:
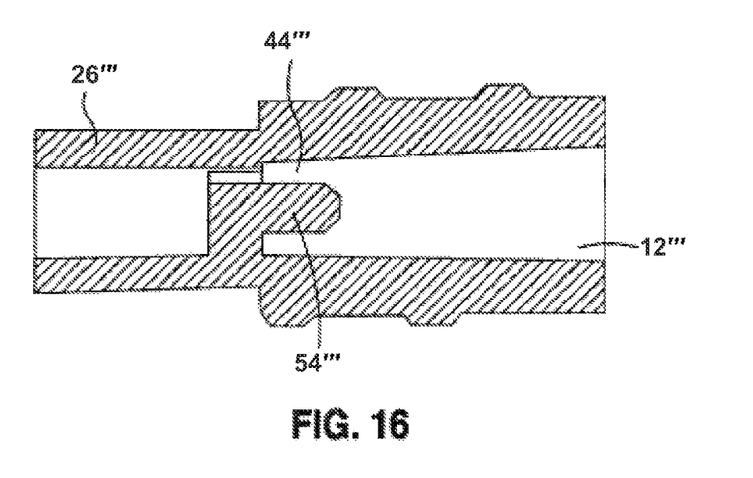
FIG. 16 is a cross-sectional view of the male and female connectors of FIGS. 14 and 15, in a connected state.

In another embodiment, shown in FIGS. 14-16, the prong 44''' of the male connector 12''' may be circumferential. The prong 44''', shown in FIG. 16, may be hollow inside its circumference such that it may still engage the groove 54 of the female connector 26'''. The groove 54''', shown in FIG. 15, of the female connector 26''' may then also be circumferential in shape so that it may receive the prong 44''' of the male connector 12'''. Additionally, as shown in FIGS. 14-15, the attachment piece 52''' of the male connector 12''' may be threaded and the ridge 56''' of the female connector 26''' may be threaded. Thus, to secure the male and female connectors 12''', 26''', the male connector 12''' may be screwed onto the female connector 26''', as shown in FIG. 16.

In sum, a connection device having a male connector and a female connector is provided. The female connector will only accommodate the dedicated male connector, thereby prohibiting a misconnection with the wrong male connector. In certain embodiments, a member prohibits male connectors other than a dedicated male connector from being fully inserted into the female connector. In certain other embodiments, a post prohibits male luers, other than a dedicated male connector including a slot, from being fully inserted into the female connector. In yet certain other embodiments, a series of prongs in the male connector and corresponding grooves in the female connector ensure the proper connection. Once the male connector is inserted and secured within the female connector, a fluid-tight seal is formed between the male connector and the female connector. The disclosed embodiments therefore prevent the misconnection of male and female luer connectors without requiring medical personnel to take additional precautionary steps.

Although the disclosed embodiments have been described and illustrated in detail, it is to be clearly understood that the same is by way of illustration and example only and is not to be taken by way of limitation.

What is claimed is:

1. A connection device comprising:
   a male connector with a distal end and a proximal end and comprising a first tube pocket configured to accept a tube at the proximal end and a plurality of prongs at the distal end, the plurality of prongs each having an opening at a distal end that is in fluid communication with the first tube pocket; and
   a female connector with a distal end and a proximal end and comprising a second tube pocket configured to accept a tube at the distal end and a cavity comprising a plurality of internal grooves configured to matingly engage the plurality of prongs of the male connector at the proximal end, the plurality of grooves each having an opening at a distal end that is in fluid communication with the second tube pocket.

2. The connection device of claim 1, wherein the male connector further comprises a snapping piece of a snap-fit connector.

3. The connection device of claim 2, wherein the female connector further comprises a ridge configured to cooperate with the snapping piece of the male connector to secure the male connector to the female connector.

4. The connection device of claim 3, wherein the snapping piece and ridge cooperate to secure the male connector to the female connector so as to form a fluid-tight seal.

5. The connection device of claim 3, wherein the male connector further comprises a wing coupled to the snapping piece, the wing configured to disengage the snapping piece from the ridge of the female connector when the wing is deformed.

6. The connection device of claim 5, wherein the male connector further comprises a notch configured to allow the snapping piece to flex open and disengage from the ridge.

7. The connection device of claim 1, wherein
the second tube pocket comprises a base and at least one standoff disposed within the second tube pocket and configured to prevent the accepted tube from forming a seal at the base of the second tube pocket.

8. The connection device of claim 1, wherein:
the male connector further comprises threads; and
the female connector further comprises threads configured to cooperate with the threads of the male connector to secure the male connector to the female connector.

* * * * *